(12) United States Patent
Knecht

(10) Patent No.: US 9,622,900 B2
(45) Date of Patent: Apr. 18, 2017

(54) KNEE BRACE WITH TOOL LESS LENGTH ADJUSTER

(75) Inventor: Steven S. Knecht, Bakersfield (CA)

(73) Assignee: Townsend Industries, Inc., Bakersfield, CA (US)

( * ) Notice: Subject to any disclaimer, the term of this patent is extended or adjusted under 35 U.S.C. 154(b) by 262 days.

(21) Appl. No.: 14/359,152

(22) PCT Filed: Sep. 14, 2012

(86) PCT No.: PCT/US2012/055411
§ 371 (c)(1),
(2), (4) Date: May 19, 2014

(87) PCT Pub. No.: WO2013/040354
PCT Pub. Date: Mar. 21, 2013

(65) Prior Publication Data
US 2014/0364782 A1  Dec. 11, 2014

Related U.S. Application Data

(60) Provisional application No. 61/535,572, filed on Sep. 16, 2011.

(51) Int. Cl.
*A61F 5/01* (2006.01)

(52) U.S. Cl.
CPC .......... *A61F 5/0125* (2013.01); *A61F 5/0123* (2013.01); *A61F 2005/0134* (2013.01); *A61F 2005/0148* (2013.01); *A61F 2005/0155* (2013.01)

(58) Field of Classification Search
CPC ............... A61F 5/0123; A61F 5/0125; A61F 2005/0181; A61F 5/01; A61F 5/0102; A61F 5/0127; A61F 5/013
USPC ....... 602/16, 5, 12, 19–30; 128/847
See application file for complete search history.

(56) References Cited

U.S. PATENT DOCUMENTS

| | | | |
|---|---|---|---|
| 4,817,588 A | 4/1989 | Bledsoe | |
| 6,347,817 B1 * | 2/2002 | Chou | B60P 7/15 248/230.6 |
| 6,381,810 B2 | 5/2002 | Hsieh | |
| 6,383,156 B1 | 5/2002 | Enzerink et al. | |
| 6,821,261 B2 | 11/2004 | Doty et al. | |
| 6,981,957 B2 | 1/2006 | Knecht et al. | |
| 7,097,627 B2 | 8/2006 | Enzerink et al. | |
| 7,127,723 B2 | 10/2006 | Endo et al. | |
| 7,128,723 B2 | 10/2006 | Doty et al. | |

(Continued)

*Primary Examiner* — Kari Rodriquez
(74) *Attorney, Agent, or Firm* — David S. Safran

(57) ABSTRACT

A knee brace which allows the same bolster pad to be used for either the right or left leg, is adjustable to compensate for the differing angle between men and women and allows individual adjustment for each patient's comfort and brace rotation for proper fit and joint alignment. These characteristics are obtained by a contoured bolster that is selectively mountable at various positions on either side of the shin cross piece depending on whether the brace is for the left or right leg, the bolster always being on the medial side of the shin to contact the flat section on the front of the shin thereby minimizing unwanted rotation of the brace. The bolster pad has a front face with a curvature matched to a curvature of an inner side of the cross piece and a flat on a rear side to contact the front of the shin.

6 Claims, 18 Drawing Sheets

(56) References Cited

U.S. PATENT DOCUMENTS

| | | | |
|---|---|---|---|
| 7,384,406 B2 | 6/2008 | Enzerink et al. | |
| 7,434,583 B2 | 10/2008 | Win | |
| 7,534,220 B2 | 5/2009 | Cormier et al. | |
| 7,918,809 B2 | 4/2011 | Enzerink et al. | |
| 8,517,965 B2 | 8/2013 | Doty et al. | |
| 2008/0032756 A1* | 2/2008 | Kanazawa | H01Q 1/243 455/575.3 |
| 2008/0306421 A1* | 12/2008 | Enzerink | A61F 5/0125 602/16 |
| 2010/0152637 A1* | 6/2010 | Wang | A61F 5/0111 602/23 |
| 2011/0082402 A1* | 4/2011 | Oddou | A61F 5/0125 602/16 |
| 2012/0289878 A1* | 11/2012 | Schwenn | A61F 5/0193 602/23 |

* cited by examiner

KNEE BRACE WITH TOOL LESS LENGTH ADJUSTER

CROSS REFERENCE TO RELATED APPLICATION

This application is a non-provisional conversion of provisional application 61/565,572.

BACKGROUND OF THE INVENTION

Field of the Invention

The present invention relates to orthopedic knee braces of the type in which at least one of the femoral arms has a length adjustment mechanism; and wherein adjustment of the length of at least one of the arms produces a medial-lateral angular movement of at least one or the other of the femoral arms.

Description of Related Art

An orthopedic knee braces of the type to which the present invention is directed is known from U.S. Pat. No. 6,981,957 of which the present inventor is a co-inventor. The length adjustment mechanism of this knee brace comprises a slide mechanism on at least one of the femoral arms which is in the form of a slotted guide and a slider which is fixable at selected locations along the length of said slotted guide by a screw that extends through the slot of the slotted guide between opposite sides of the respective femoral arm. Thus, a tool is required to be able to adjust from one to four screws depending on the embodiment of the slider and whether one or both femoral arms is equipped with a length adjustment mechanism.

U.S. Pat. No. 7,534,220, entitled "Adjustable Ergonomic Brace", assigned to OSSUR HF discloses an ergonomic knee brace that includes an upper strut for extending along an upper leg, and a lower strut for extending along a lower leg, each of which has a length adjustment mechanism comprised of telescopic slide mechanism in which a screw-in knob that engages receiving holes in the struts is used to fix the length once set. Thus, a tool is not required to fix or release the length adjustment mechanism. However, if the screw knob is not sufficiently tightened or if it backs off in use, the slide of the length adjustment mechanism can become free to move.

U.S. Pat. No. 7,128,723, entitled "Orthopedic brace having length-adjustable supports", assigned to DJ Orthopedics, LLC discloses an orthopedic brace that includes a first length-adjustable support, a second length-adjustable support and a spring-biased button for length adjustment. Each length adjustable support includes a longitudinal channel and a sliding upright within the channel. Each sliding upright includes multiple through-holes and a floor of each channel includes the spring-biased button. The spring-biased button further includes retaining tabs on a lower end. An operator depresses the button and then the retaining tabs on the lower end of the button extend through holes. The button is engageable with each hole such that the button positively locks a position of the upright with respect to the channel. The upright is slidable within the channel when the button is depressed. However, such a mechanism poses the disadvantage that contact of the button with an object, such as the leg of a table, can cause inadvertent release.

SUMMARY OF THE INVENTION

It is an object of the present invention to improve upon length adjustment mechanisms of the above mentioned knee braces so as to enable adjustment of the length of the femoral arm(s) without the use of tools, and in a simple manner that is unlikely to release the adjustment mechanism, in use.

This object is achieved by the provision of a length adjustment mechanism comprising an over toggling lock mechanism having a circular detent plate with spring arms and a lever for engaging the detents of the detent plate in notches of a strut. In particular, a pressing action of the lever pushes the circular detent plate causing the spring arms to be compressed so that the detents move into semicircular notches of the strut for preventing the axial movement of the strut (locked position), and releasing of the lever enables the spring arms to lift the detents out of the notches for enabling axial adjustment (released position).

DETAILED DESCRIPTION OF THE INVENTION

Figure 1:
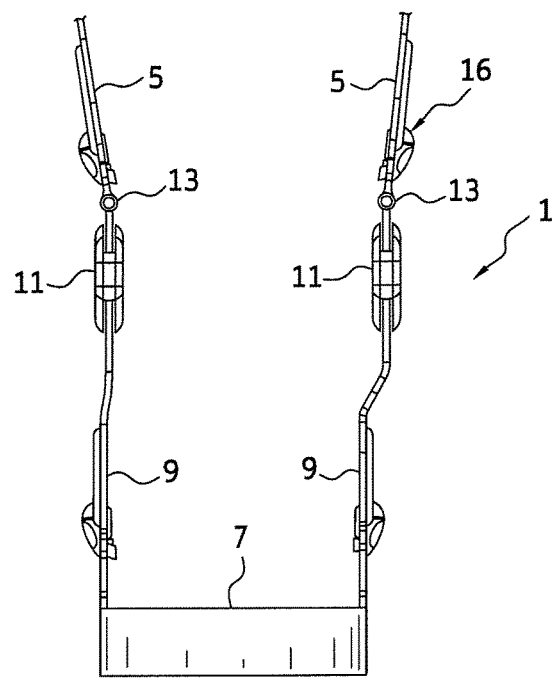
FIG. 1 is a partial, front elevational view of a knee brace in accordance with the length adjustment mechanism of the invention with all posterior straps removed.
Figure 2:
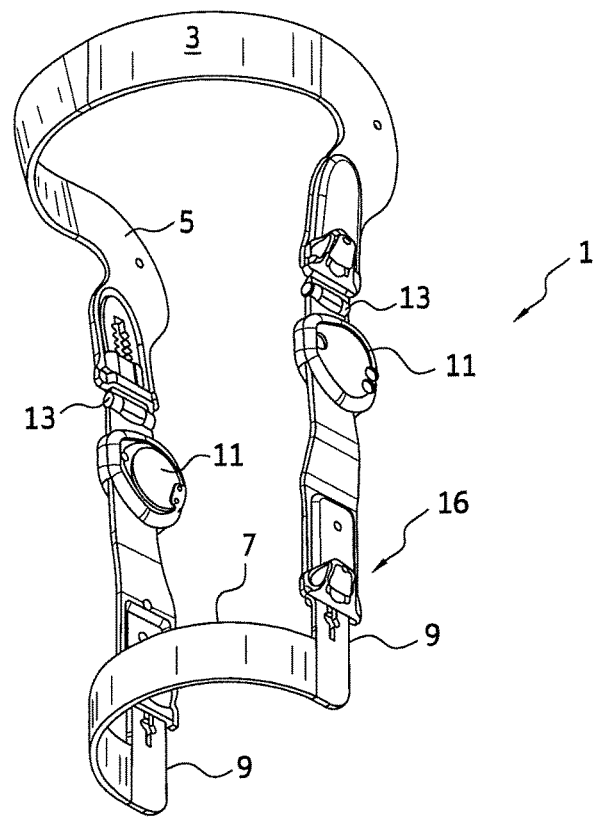
FIG. 2 is a front perspective view of a knee brace in accordance with the length adjustment mechanism of the invention with all posterior straps removed.

At the outset, it is noted that the orthotic knee brace shown in the drawings is merely an illustrative example and the following description of the invention should be viewed as applicable to numerous other types of knee braces, such as that of the above mentioned U.S. Pat. Nos. 6,981,957, 7,128,723 and 7,534,220. As can be seen in the drawings, as is typical, the knee brace 1 has an upper cross piece 3 connecting the medial and lateral femoral arms 5, a lower cross piece 7 connecting the medial and lateral tibial arms 9, and a polycentric hinge mechanism 11 connecting the lateral femoral and tibial arms and connecting the medial femoral and tibial arms. Furthermore, like U.S. Pat. No. 6,981,957, unicentric hinges 13 are disposed between the polycentric hinge mechanism and the femoral arm 5. Not shown are the upper and lower posterior straps that connect to medial and lateral sides of the cross pieces and/or medial and lateral femoral and tibial arms to hold the brace on the wearer's leg.

In the above context, the length adjuster mechanism 16 of the present invention will now be described.

Figure 3:
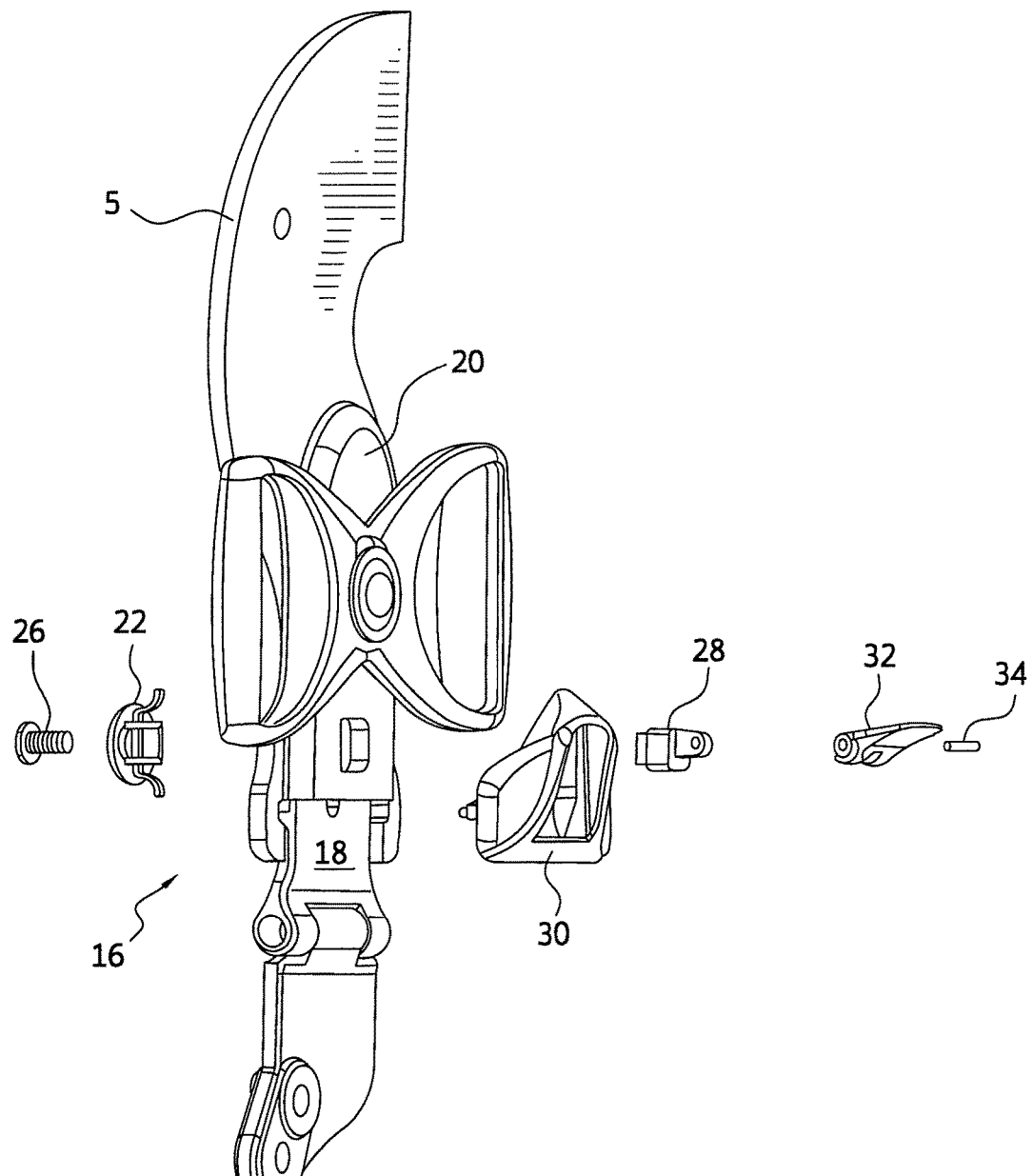
FIG. 3 is a partially exploded perspective view of an locked.
Figure 4:
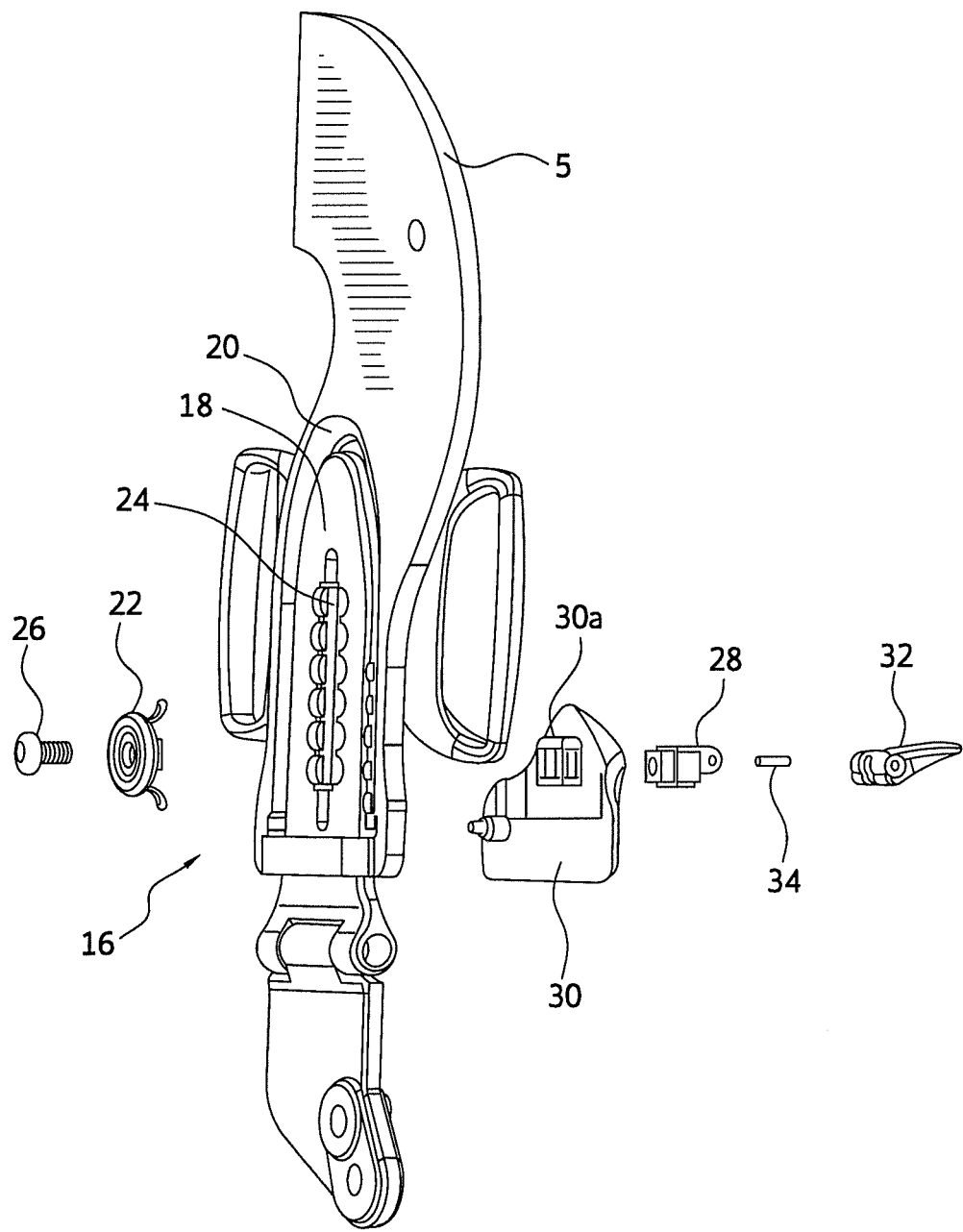
FIG. 4 is a partially exploded perspective view of an inner side of the length adjustment mechanism of the invention.
Figure 16:
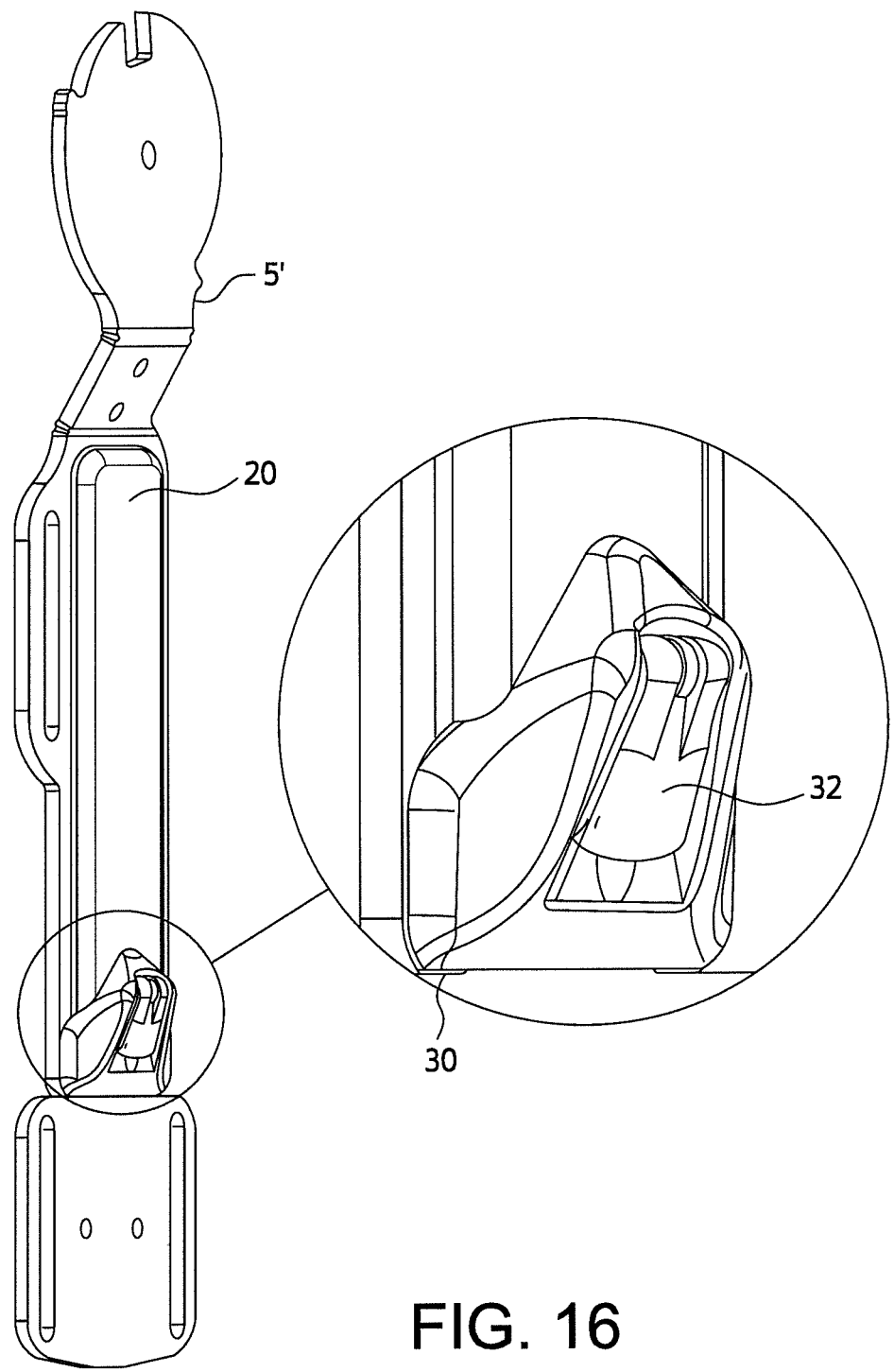
FIG. 16 is a perspective view of the outer side of a modified length adjuster mechanism for a post operative brace with an enlarged detail of the lock mechanism in the locked position.

From FIGS. 3 & 4, principal elements of the length adjuster mechanism 16 can be seen. Shown there are a slide 18 which is slidable in a receiver 20 of the femoral arm 5, a detent element 22 that is received in the track 24 of the slide 18, being secured by a screw 26 to the link 28, the link 28 being movably received in a through opening 30a of a surround 30 and being coupled to a toggle mechanism having a lock lever 32 by a spring pin 34. Also shown is a double handle arrangement 36, which is optional and has been omitted from the length adjuster mechanism of the post operative brace shown in FIGS. 16 & 17.

Figure 15:
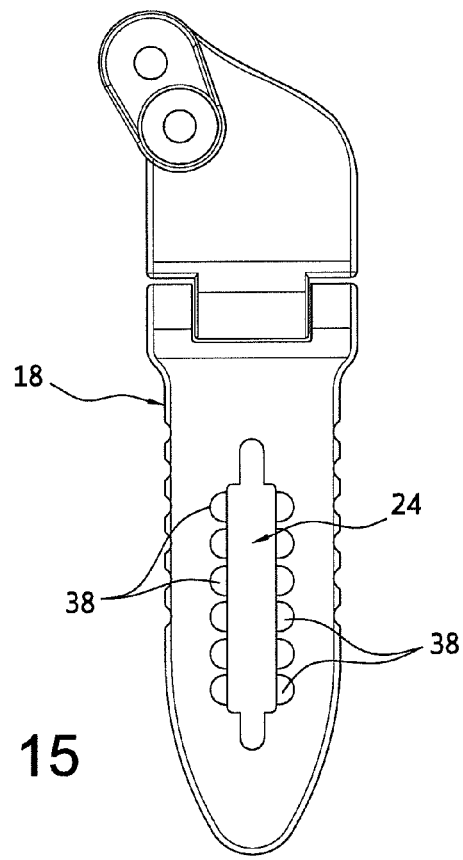
FIG. 15 is an inner side view of the joint element connected to the slide element of the length adjuster mechanism.

As can be seen in FIG. 12, the detent element 22 is comprised of a plate 22a, a through hole 22b in which the link is held by the screw 26, a pair of detents 22c, and a pair of spring fingers 22d. FIG. 13 shows the threaded opening 28a into which screw 26 is threaded and a hole 28b for the spring pin 34 that connects it to the lock lever 32. FIG. 14 shows the receivers 32a for the spring pin 34. These receivers have an eccentric 32b formed thereon. As is apparent from FIG. 15, the track 24 is flanked by a line of recesses 38. These recesses are matched to the detents 22c of the detent element 22 while the track 24 is sized and shaped to guide the surfaces of the walls forming the through hole 22b from which the detents 22c extend outward.

Figure 5:
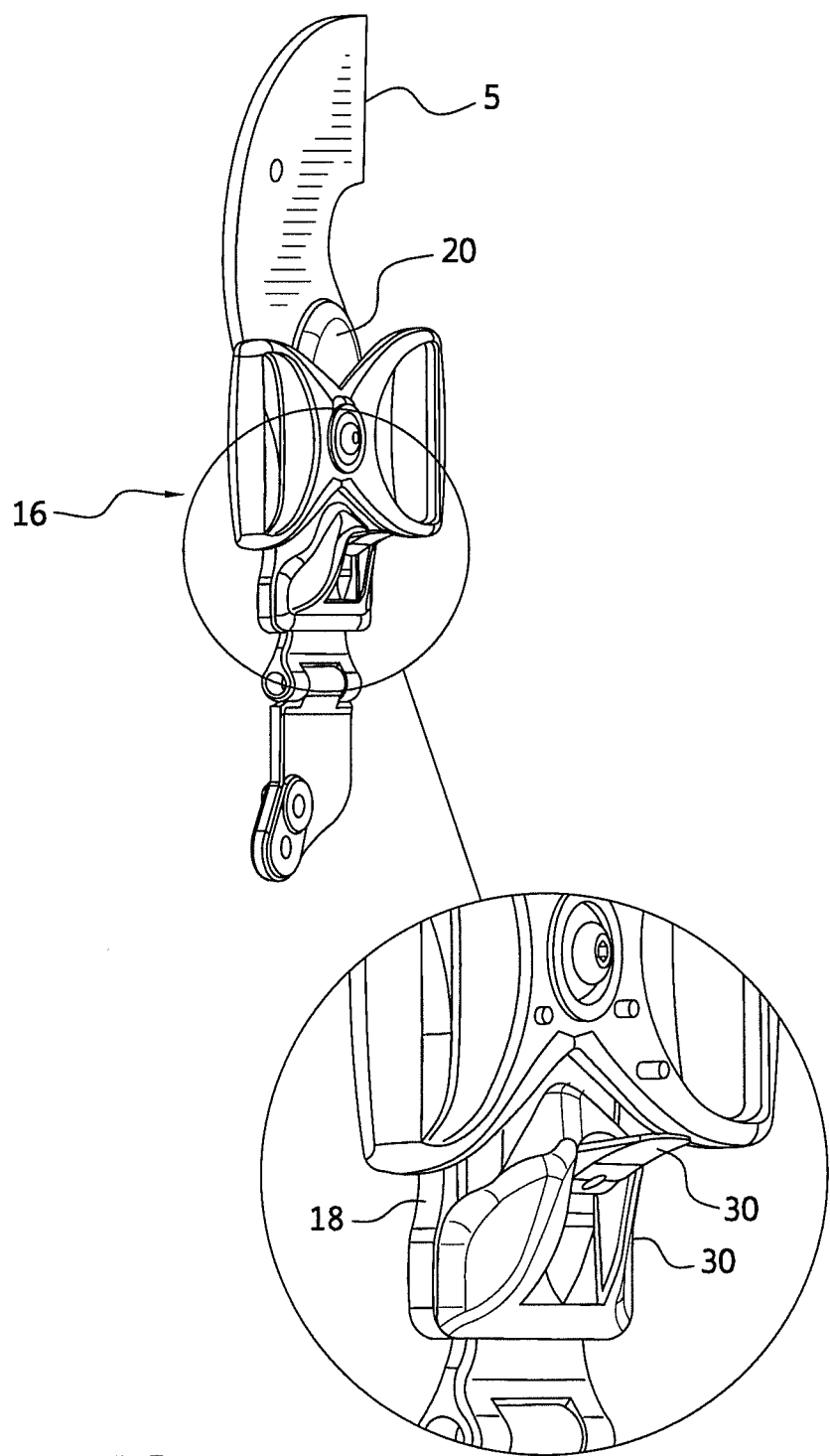
FIG. 5 is a view similar to that of FIG. 3, showing an enlarged detail of the lock mechanism in the released position.
Figure 6:
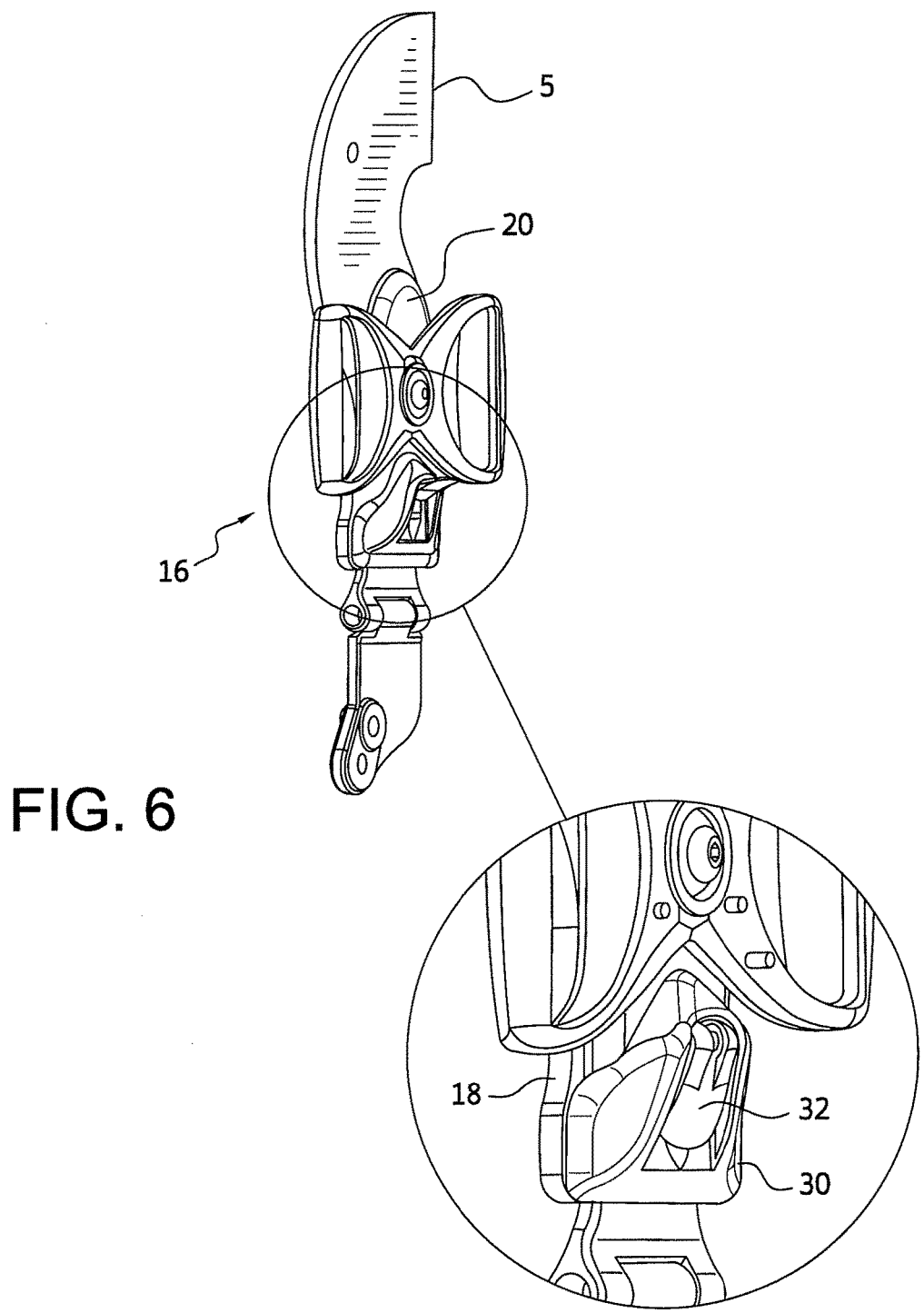
FIG. 6 is a view similar to that of FIG. 3, showing an enlarged detail of the lock mechanism in the locked position.

When the lock lever 32 is lifted into the FIG. 5 position, the eccentrics 32b move off of the link 28 allowing the spring fingers 22d to lift the detent element 22, thereby disengaging the detents 22c from the recesses 38 (FIG. 7) and allowing the slide 18 to be moved within the receiver 20. However, when the lever 32 is swung from the FIG. 5 position into the FIG. 6 position, the eccentrics 32c cause the link 28 to be pulled outward, thereby causing it to pull the detent element 22 against the force of the spring fingers 22d and compressing them so that the detents 22c become engaged in a pair of recesses 38 (FIG. 8). Due to the over top dead center toggling of the lever, it is held in place and the engagement of the detents secured. In the locked position, because of its positioning within the surround 30, inadvertent releasing of the lock is precluded.

Figure 17:
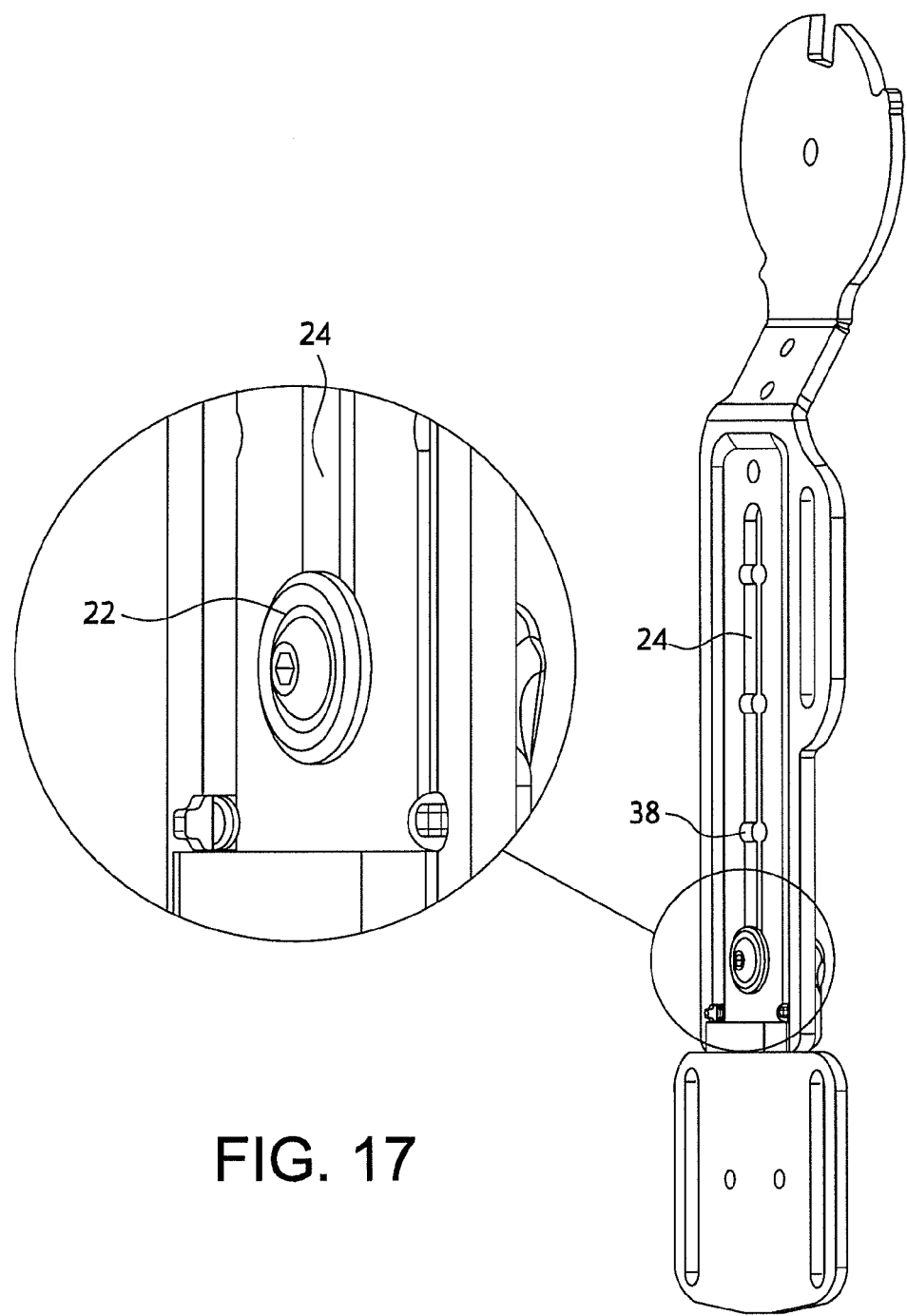
FIG. 17 is a perspective view of the inner side of the modified length adjuster mechanism FIG. 16 with an enlarged detail of the lock mechanism in the locked position.

As mentioned previously, FIGS. 16 & 17 show a modified length adjustment mechanism 16 which operationally is identical to that already described. The primary differences in this embodiment are the mentioned lack of the optional handles and the fact that the femoral arm 5' that is differently configured for use in a post operative brace. FIG. 17 also shows that, when finer adjustment is not required, fewer recesses 38 can be provided.

Figure 18:
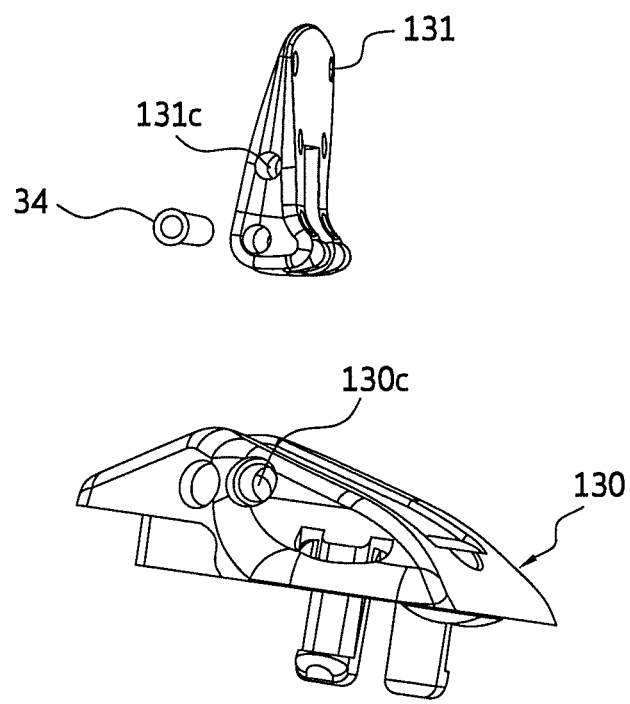
FIG. 18 is an exploded view of a modified version of the surround of the lock mechanism shown in FIGS. 11(a) & 11(b) with a modified version of the lock lever of the lock mechanism shown in FIGS. 14(a)-14(d)

FIG. 18 shows a modified surround 130 with a toggle mechanism having a modified lock lever 131 for the lock mechanism. Surround 130 and lock lever 131 differ primarily from those shown in FIGS. 11(a) & 11(b) and 14(a)-14(d), respectively in the provision of an opening 131c in the lock lever 131 and a cooperating opening 130c in the surround 130 for fixing the length of the length of the adjuster mechanism 116 once it has been set by the physician. In particular, when the lock lever 131 is in the down position (shown, e.g., in FIGS. 6 & 16) locking the adjuster in the position set, a screw can be fastened extending through the opening 130c of the surround 130 into the opening 131c in the lock lever 131, thereby preventing the lock lever 131 from being raised and the position of the adjuster set by the physician from being reset accidentally or by the user.

Figure 19:
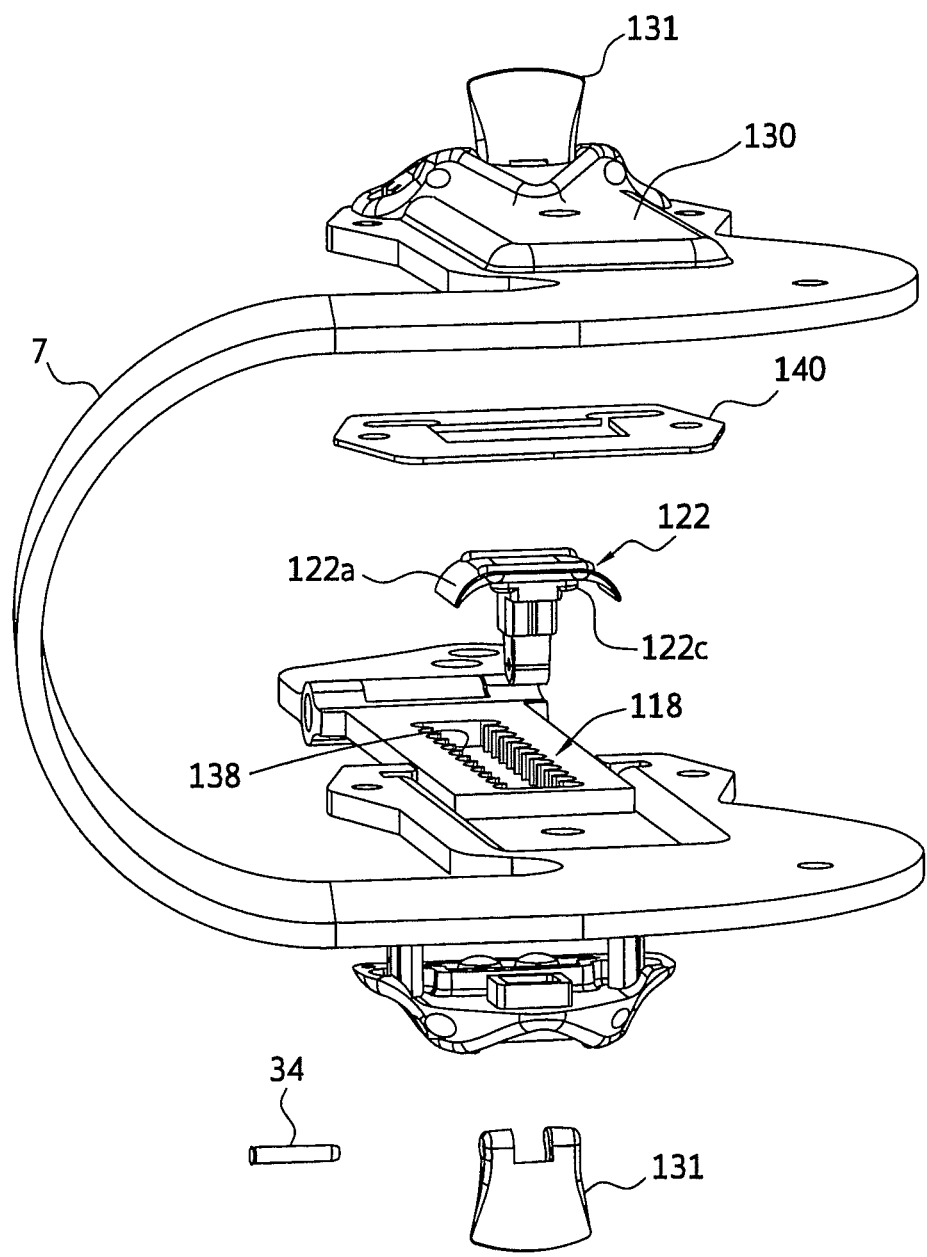
FIGS. 19 & 20 are perspective views of the inner side and outer sides of another modified length adjuster.
Figure 20:
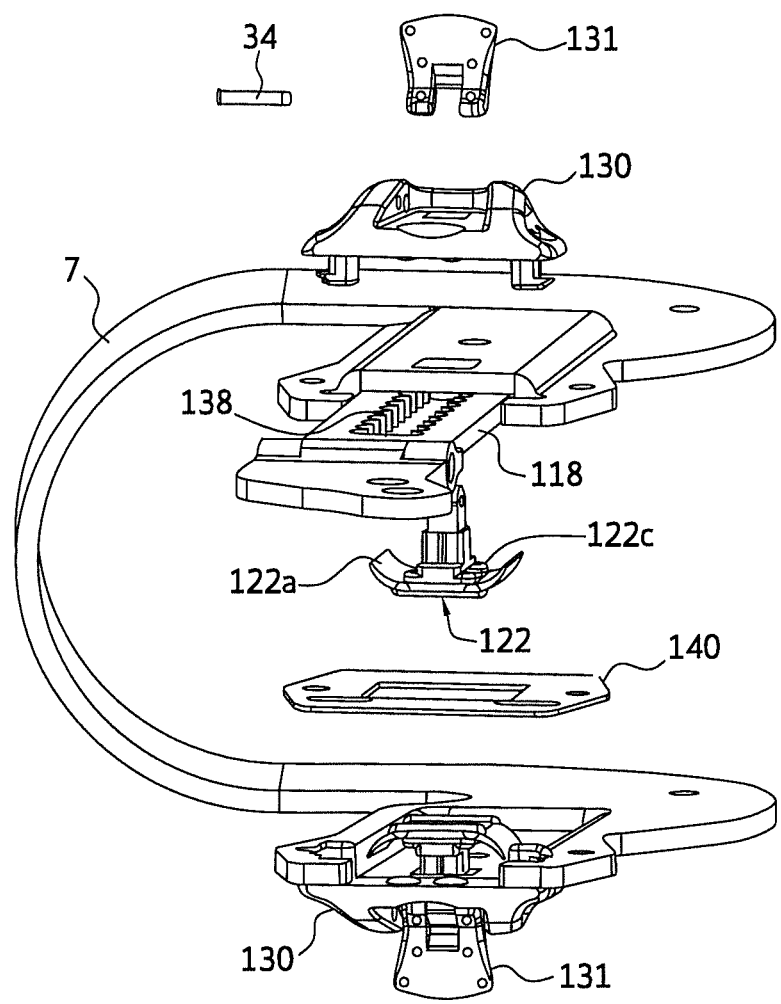

FIGS. 19 & 20 are perspective views of the inner side and outer sides of another modified length adjuster which is operationally identical to those already described. The primary differences in this embodiment are in the nature of the slide 118, detent element 122 and the provision of a cover plate for the receiver 120.

Figure 7:
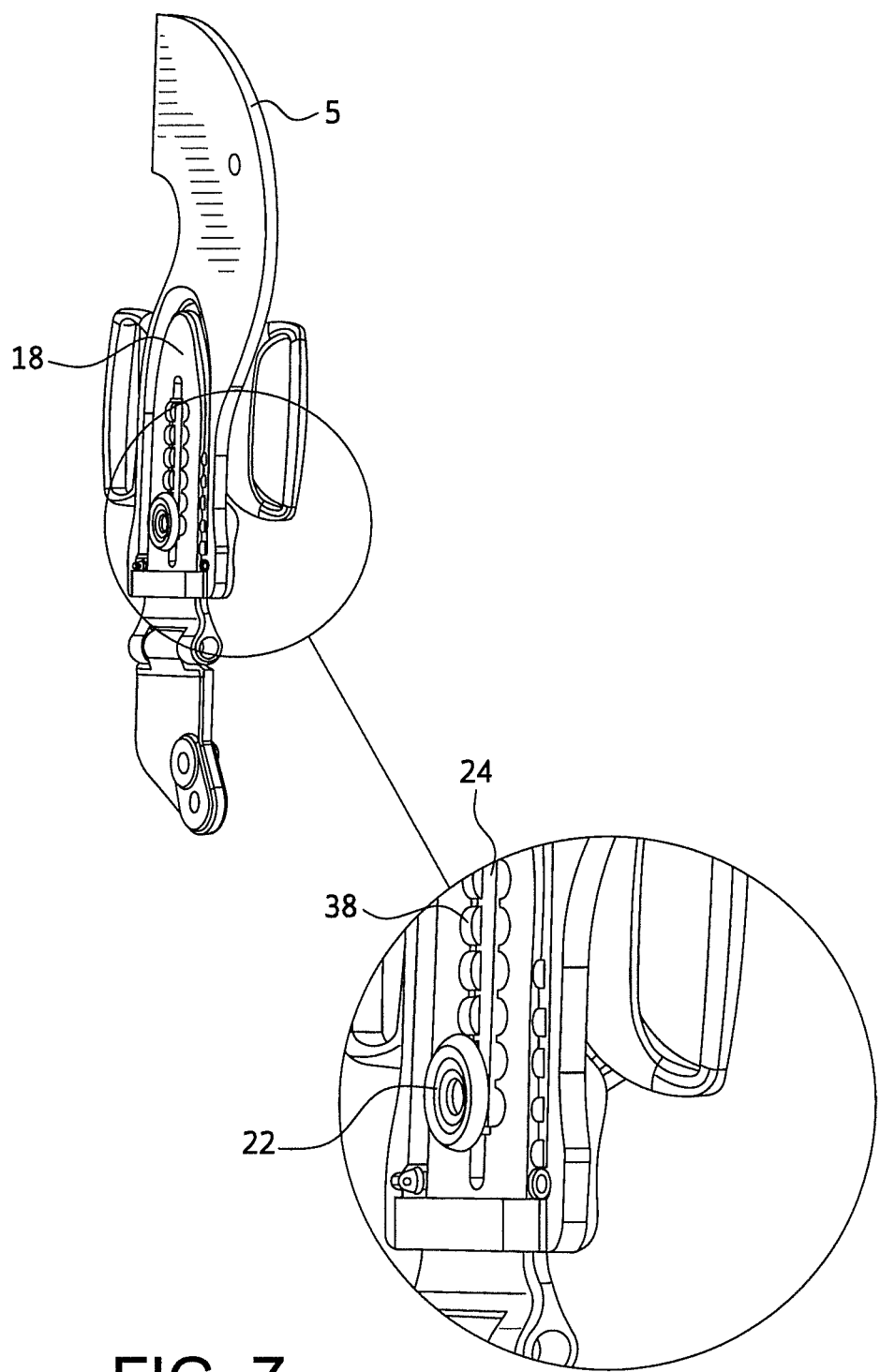
FIG. 7 is a view similar to that of FIG. 4, showing an enlarged detail of the length adjuster mechanism in the released position.
Figure 8:
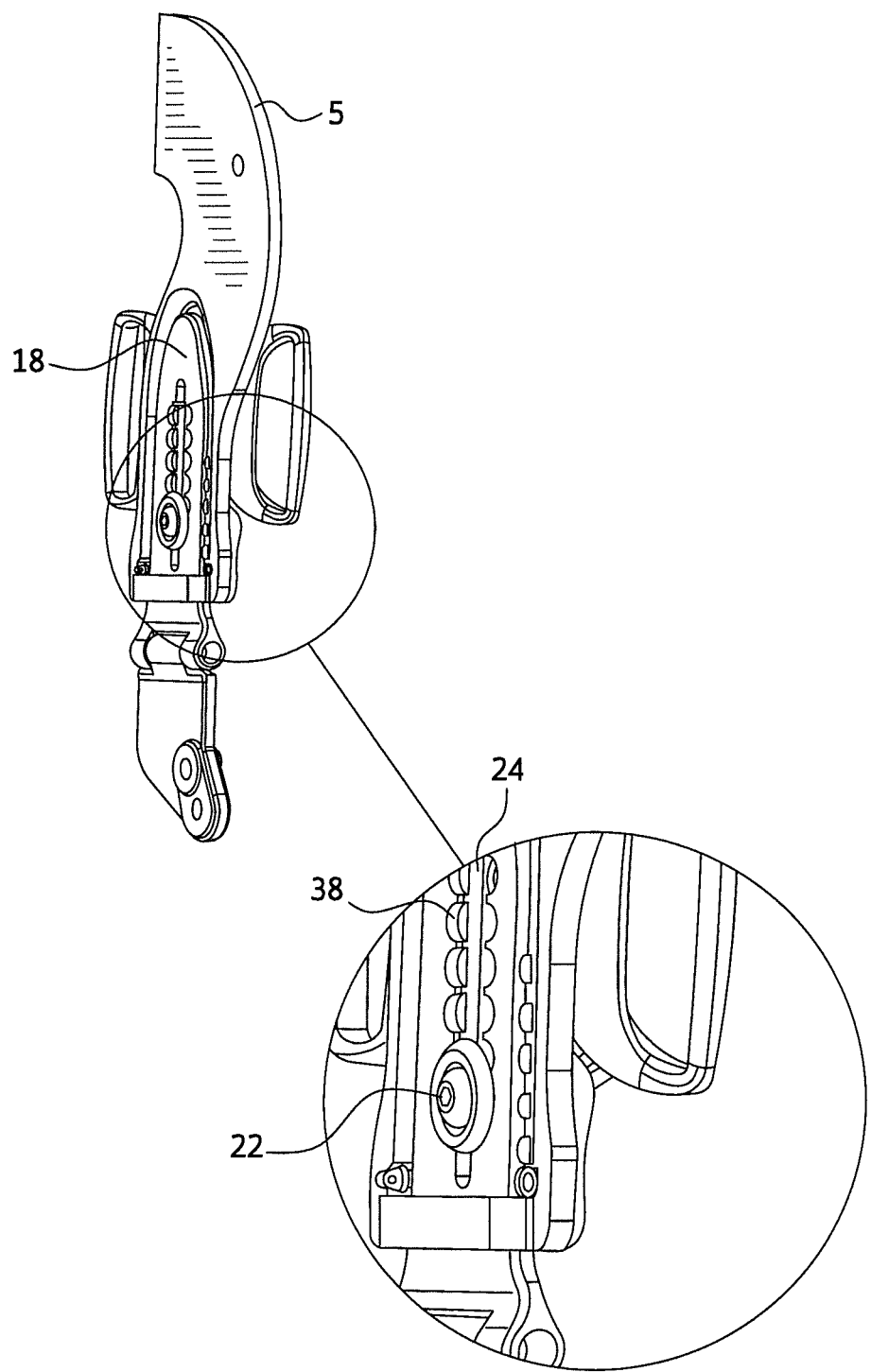
FIG. 8 is a view similar to that of FIG. 4, showing an enlarged detail of the length adjuster mechanism in the locked position.
Figure 9C:
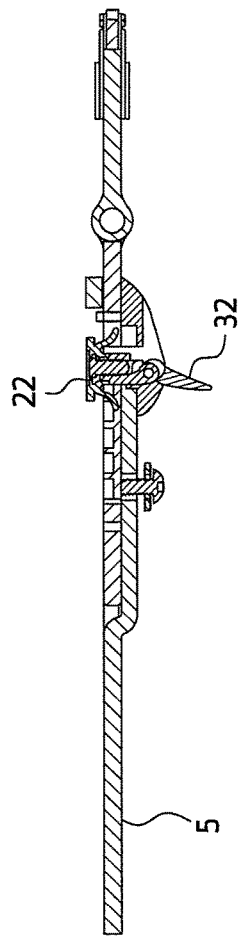
FIGS. 9A-9C are an elevational view of the length adjuster mechanism in the released position, a sectional view taken along line A-A of FIG. 9A and a sectional view taken along line B-B of FIG. 9A, respectively.
Figure 9A:
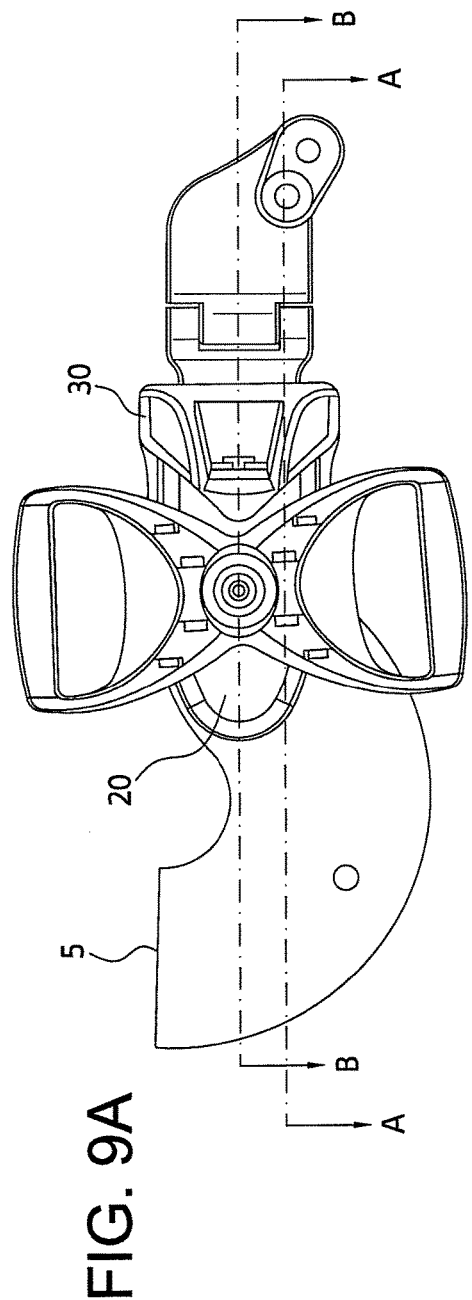
Figure 9B:
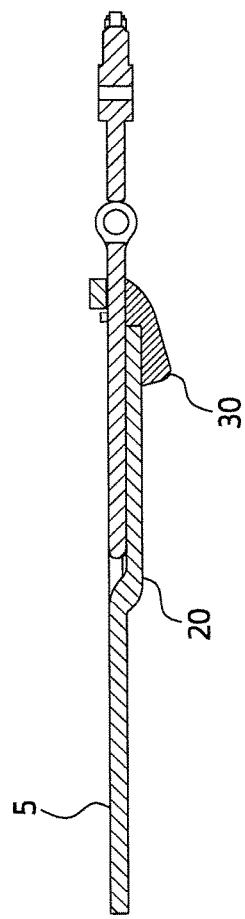
Figure 10C:
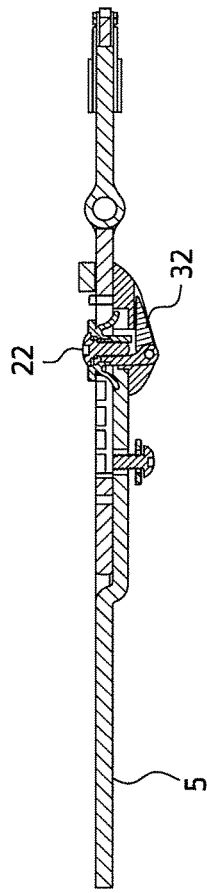
FIGS. 10A-10C are an elevational view of the length adjuster mechanism in the locked position, a sectional view taken along line C-C of FIG. 10A and a sectional view taken along line D-D of FIG. 10A, respectively.
Figure 10A:
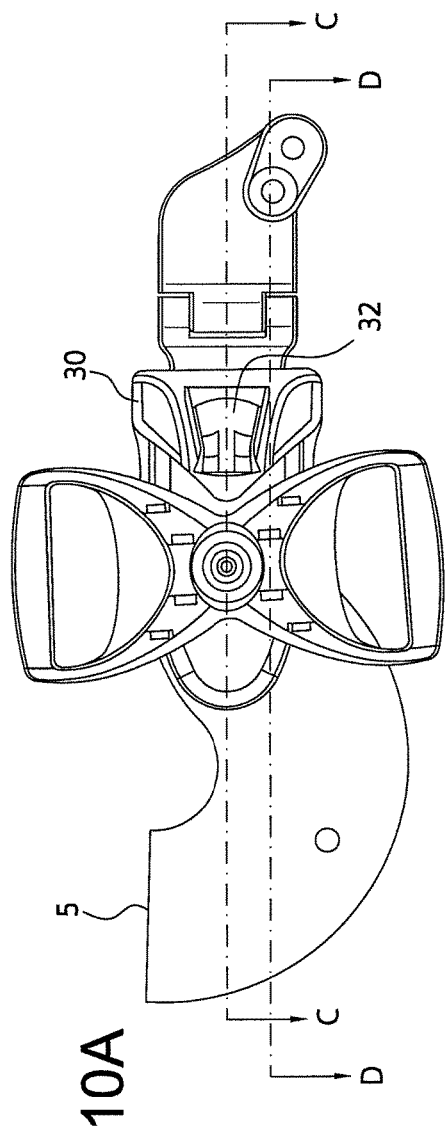
Figure 10B:
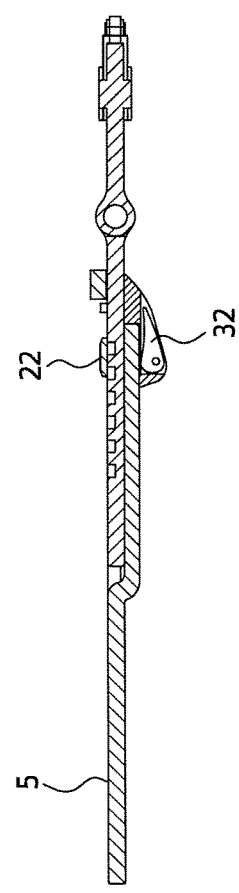
Figure 11A:
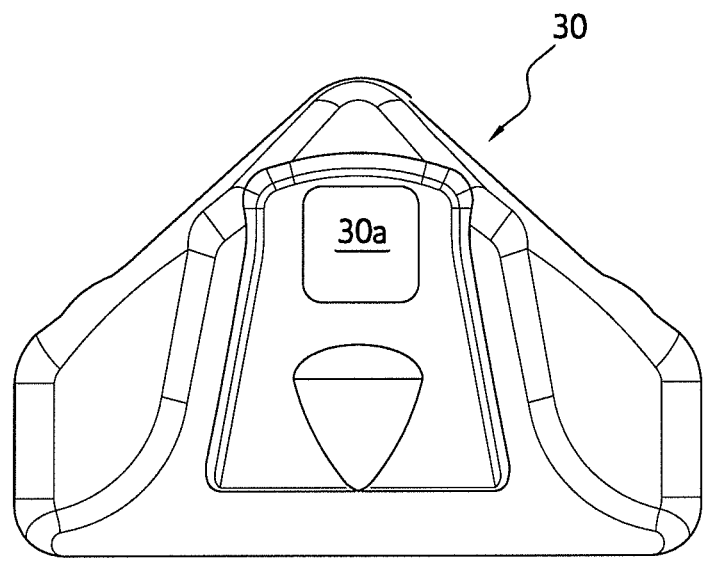
FIGS. 11(a) & 11(b) are plan and side views of a surround of the lock mechanism.
Figure 11B:
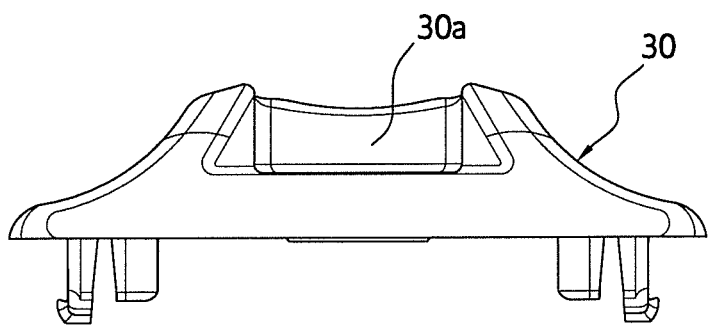
Figure 12A:
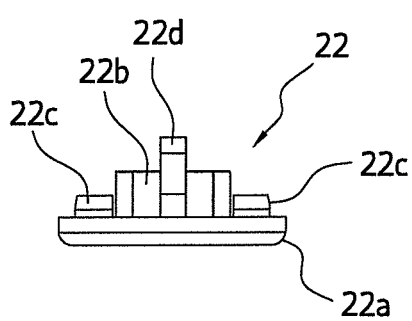
FIGS. 12(a)-12(d) are a side view in the direction of the spring fingers of the detent member of the lock mechanism, a perspective view of the detent member, a top plan view of the detent member, and a side view in a direction 90° relative to the direction of the spring fingers, respectively.
Figure 12B:
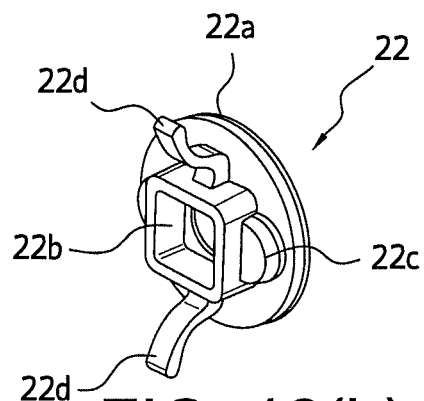
Figure 12C:
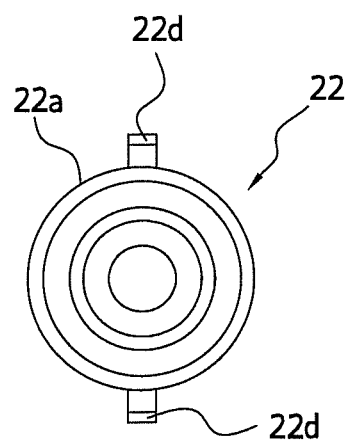
Figure 12D:
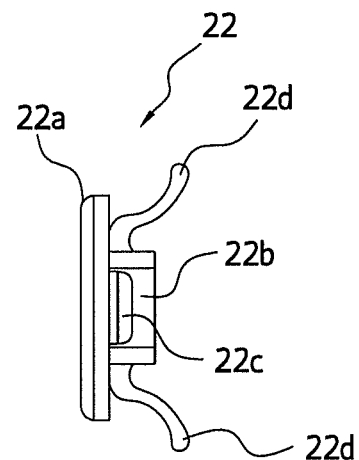
Figure 13A:
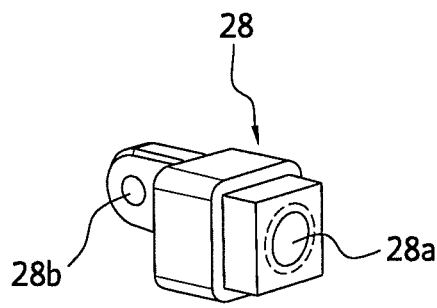
FIGS. 13(a)-13(d) are a perspective view of a link member of the lock mechanism, a side view of the link member, an end view looking toward a connector of the link member, and a top plan view of the link member.
Figure 13B:
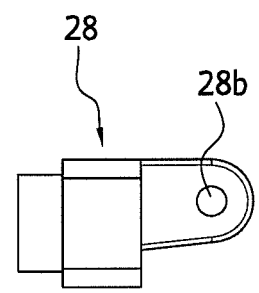
Figure 13C:
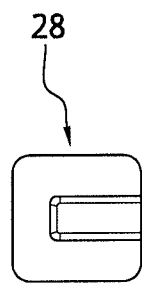
Figure 13D:
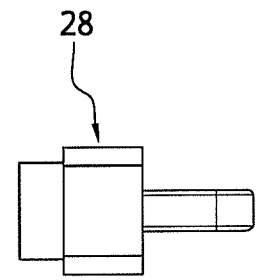
Figure 14A:
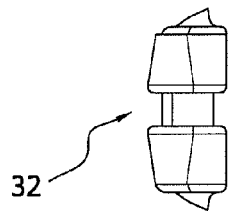
FIGS. 14(a)-14(d) are hinge end, top plan, perspective and side views of a lock lever of the lock mechanism.
Figure 14B:
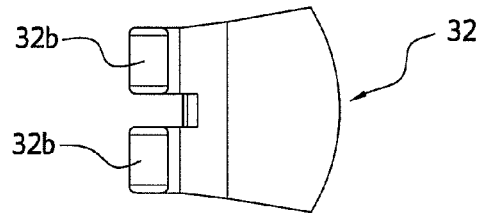
Figure 14C:
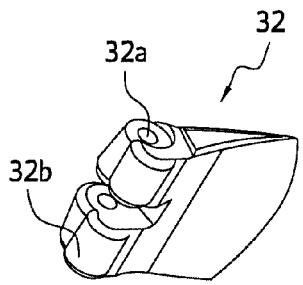
Figure 14D:
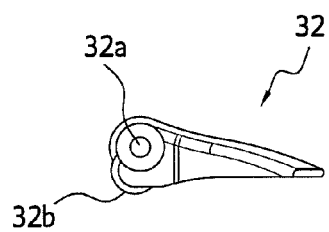

First, to more fully stabilize the slide 118, instead of a bracket as shown, e.g., in FIGS. 4, 7 & 8, in this preferred arrangement, a cover plate 140 attaches to the femoral arm 5 extending over the receiver 120 creating a channel within which the slide 118 is movable and minimizing flexing due to the tension applied when the lock lever 131 pulls on the detent element 122.

Additionally, the configuration of detent element 122 differs from that shown in FIG. 12, plate 122a being rectangular instead of round and instead of spring fingers 22d projecting from the side of walls bounding hole 22b, curved plate-shaped members are formed as extensions of the plate 122a. Such a construction is easier to produce and an effect means for lifting the detents 122c out of engagement with the recesses 138 of the slide 118. In this regard, as can be seen most easily in FIG. 20, instead of on large semicircular detent 22c as shown in FIG. 12, detent element 122 is provided with several smaller detents 122c which are engageable with the complementary, smaller recesses 138 of the slide 118, thereby providing a finer degree of adjustability.

What is claimed is:

1. In a knee brace in which at least one of a pair of femoral arms has a length adjustment mechanism, the improvement comprising said length adjustment mechanism comprising:
   a slide connected to a first part of said at least one of the femoral arms, said slide having a track with pairs of detent recesses spaced along a length thereof,
   a receiver connected to a second part of said at least one of the femoral arms and in which said slide is displaceable in a lengthwise direction for changing the length of said at least one of the femoral arms, a detent element that is received in the track of the slide, said detent element having at least one pair of detents that is engageable in at least one pair of detent recesses for fixing a position of the first and second parts of said at least one of femoral arms relative to each other, and a toggle mechanism connected to said detent element and having a locking lever with a first position in which the at least one pair of detents is locked in engagement within said at least one pair of detent recesses, and a second position releasing said at least one pair of detents for movement out of engagement with at least one pair of detent recesses for enabling adjustment of the length of said at least one of the femoral arms, said locking lever executing an over top dead center movement from said second position into said first position so as to hold the detents against inadvertent movement out of said first position, wherein said locking lever is movable relative to said detent element and only moves said detent element in a direction toward the slide when the locking member is moved from said second position to said first position.

2. In the knee brace according to claim 1, wherein said at least one pair of detent recesses comprises a plurality of pairs of detent recesses with which said at least one pair of detents are engageable.

3. In the knee brace according to claim 1, further comprising a cover plate attached to the second part of said at least one of femoral arms so as to overlie said receiver in a manner forming a channel within which the slide is movable.

4. In a knee brace in which at least one of a pair of femoral arms has a length adjustment mechanism, the improvement comprising said length adjustment mechanism comprising:

a slide connected to a first part of said at least one of the femoral arms, said slide having a track with pairs of detent recesses spaced along a length thereof, a receiver connected to a second part of said at least one of the femoral arms and in which said slide is displaceable in a lengthwise direction for changing the length of said at least one of the femoral arms, a detent element that is received in the track of the slide, said detent element having at least one pair of detents that is engageable in at least one pair of detent recesses for fixing a position of the first and second parts of said at least one of femoral arms relative to each other, and a toggle mechanism connected to said detent element and having a locking lever with a first position in which the at least one pair of detents is locked in engagement within said at least one pair of detent recesses, and a second position releasing said at least one pair of detents for movement out of engagement with at least one pair of detent recesses for enabling adjustment of the length of said at least one of the femoral arms, said locking lever executing an over top dead center movement from said second position into said first position so as to hold the detents against inadvertent movement out of said first position, wherein said detent element has biasing members engageable with said slide for forcing said detents out of engagement with said detent recesses when the locking lever of the toggle mechanism is moved into said second position.

5. In the knee brace according to claim 4, wherein said biasing members comprises spring fingers or plate-shaped members connected to said detent element.

6. In a knee brace in which at least one of a pair of femoral arms has a length adjustment mechanism, the improvement comprising said length adjustment mechanism comprising:

a slide connected to a first part of said at least one of the femoral arms, said slide having a track with pairs of detent recesses spaced along a length thereof, a receiver connected to a second part of said at least one of the femoral arms and in which said slide is displaceable in a lengthwise direction for changing the length of said at least one of the femoral arms, a detent element that is received in the track of the slide, said detent element having at least one pair of detents that is engageable in at least one pair of detent recesses for fixing a position of the first and second parts of said at least one of femoral arms relative to each other, and a toggle mechanism connected to said detent element and having a locking lever with a first position in which the at least one pair of detents is locked in engagement within said at least one pair of detent recesses, and a second position releasing said at least one pair of detents for movement out of engagement with at least one pair of detent recesses for enabling adjustment of the length of said at least one of the femoral arms, said locking lever executing an over top dead center movement from said second position into said first position so as to hold the detents against inadvertent movement out of said first position, wherein the toggle mechanism is movably connected to the detent element, the locking lever being configured to pull the detent toward the slide when the locking lever is moved from the second position to the first position.

* * * * *